US00PP33813P2

(12) United States Plant Patent
Pieters

(10) Patent No.: US PP33,813 P2
(45) Date of Patent: Jan. 4, 2022

(54) ***CHRYSANTHEMUM* PLANT NAMED 'G21VIG05DY'**

(50) Latin Name: ***Chrysanthemum* X *morifolium***
Varietal Denomination: G21VIG05DY

(71) Applicant: Elien Sofie Pieters, Oostnieuwkerke (BE)

(72) Inventor: Elien Sofie Pieters, Oostnieuwkerke (BE)

(73) Assignee: PARATY B.V.B.A., Oostnieuwkerke (BE)

( * ) Notice: Subject to any disclaimer, the term of this patent is extended or adjusted under 35 U.S.C. 154(b) by 0 days.

(21) Appl. No.: 17/186,318

(22) Filed: Feb. 26, 2021

(51) Int. Cl.
*A01H 5/02* (2018.01)
*A01H 6/14* (2018.01)

(52) U.S. Cl.
USPC ..... Plt./289
CPC ..... *A01H 6/1424* (2018.05)

(58) Field of Classification Search
USPC ..... Plt./289
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Chrysanthemum* plant named 'G21VIG05DY', characterized by its upright, outwardly spreading and uniformly rounded plant habit; vigorous growth habit; freely branching habit; dense and full plant habit; flexible stems; dark green-colored leaves; uniform and freely flowering habit; long flowering period; medium-sized decorative type inflorescences with ray florets that are golden yellow in color; and excellent garden performance.

1 Drawing Sheet

Figure 2:
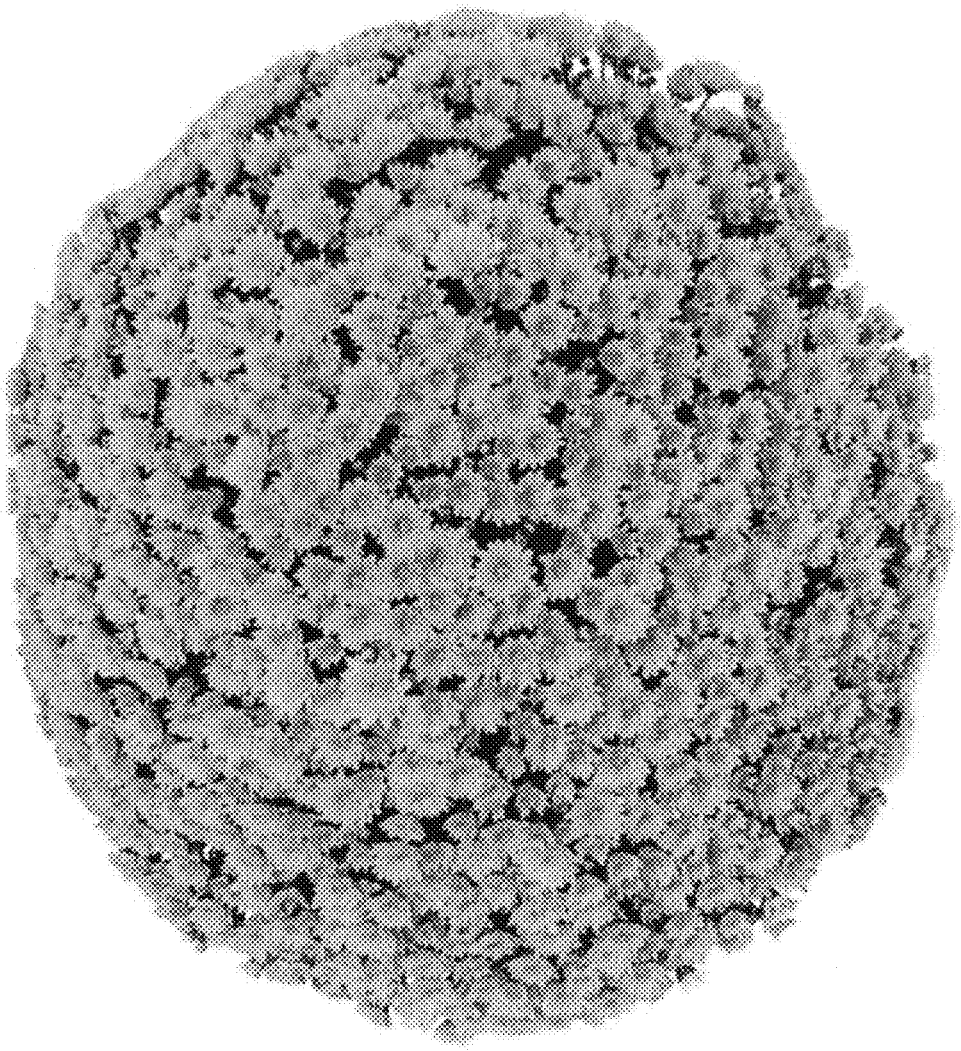

Botanical designation: *Chrysanthemum* X *morifolium*.
Cultivar denomination: 'G21VIG05DY'.

STATEMENT REGARDING PRIOR DISCLOSURES BY INVENTOR/APPLICANT

An European Community Plant Breeder's Rights application for the instant plant was filed by the Assignee, Paraty B.V.B.A. of Oostnieuwkerke, Belgium on Dec. 19, 2019, application number 2019/3464. Foreign priority is not claimed to this application.

There have been no offers for sale anywhere in the world prior to the effective filing date of this Application and no accessibility to one of ordinary skill in the art.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* X *morifolium* and hereinafter referred to by the name 'G21VIG05DY'.

The new *Chrysanthemum* plant is a product of a planned breeding program conducted by the Inventor in Oostnieuwkerke, Belgium. The objective of the breeding program is to create new uniformly mounding and freely flowering *Chrysanthemum* plants with unique and attractive inflorescence form and ray floret coloration.

The new *Chrysanthemum* plant is a naturally-occurring whole plant mutation of *Chrysanthemum* X *morifolium* 'Vigorelli Violet', disclosed in U.S. Plant Pat. No. 23,965. The new *Chrysanthemum* plant was discovered and selected by the Inventor as a single flowering plant from within a population of plants of 'Vigorelli Violet' in a controlled greenhouse environment in Oostnieuwkerke, Belgium in October, 2017.

Asexual reproduction of the new *Chrysanthemum* plant by vegetative terminal cuttings was first conducted in a controlled greenhouse environment in Oostnieuwkerke, Belgium in January, 2018. Asexual reproduction by vegetative terminal cuttings has shown that the unique features of this new *Chrysanthemum* plant are stable and reproduced true to type in successive generations.

SUMMARY OF THE INVENTION

The following traits have been repeatedly observed and are determined to be the unique characteristics of 'G21VIG05DY'. These characteristics in combination distinguish 'G21VIG05DY' as a new and distinct *Chrysanthemum* plant:

1. Upright, outwardly spreading and uniformly rounded plant habit; vigorous growth habit.
2. Freely branching habit; dense and full plant habit; flexible stems.
3. Dark green-colored leaves.
4. Uniform and freely flowering habit.
5. Long flowering period.
6. Medium-sized decorative type inflorescences with ray florets that are golden yellow in color.
7. Excellent garden performance.

Plants of the new *Chrysanthemum* can be compared to plants of the mutation parent, 'Vigorelli Violet'. In side-by-side comparisons, plants of the new *Chrysanthemum* differ primarily from plants of 'Vigorelli Violet' in ray floret color as ray florets of plants of the new *Chrysanthemum* are golden yellow in color whereas ray florets of plants of 'Vigorelli Violet' are dark red purple in color becoming lighter red purple with development giving a bi-colored appearance.

Plants of the new *Chrysanthemum* can also be compared to plants of *Chrysanthemum* X *morifolium* 'PPP COL OR07', disclosed in U.S. Plant Pat. No. 20,355. In side-by-side comparisons, plants of the new *Chrysanthemum* differ primarily from plants of 'PPP COL OR07' in the following characteristics:

1. Plants of the new *Chrysanthemum* are smaller and not as vigorous as plants of 'PPP COL OR07'.
2. Leaves of plants of the new *Chrysanthemum* are brighter green in color than leaves of plants of 'PPP COL OR07'.
3. Plants of the new *Chrysanthemum* flower later than plants of 'PPP COL OR07'.
4. Ray florets of plants of the new *Chrysanthemum* are golden yellow in color whereas ray florets of plants of 'PPP COL OR07' are bronze in color with darker red centers.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. The photograph comprises a top perspective view of a typical flowering plant of 'G21VIG05DY' grown in a container.

DETAILED BOTANICAL DESCRIPTION

The aforementioned photograph and following observations and measurements describe plants grown in 19-cm containers in an outdoor nursery in Oostnieuwkerke, Belgium under natural daylengths during the autumn and employing cultural practices typically used in commercial *Chrysanthemum* production. During the production of the plants, day temperatures ranged from 20° C. to 25° C. and night temperatures ranged from 12° C. to 18° C. Plants were 20 weeks old when the photograph and detailed description were taken. In the following description, color references are made to The Royal Horticultural Society Colour Chart, 2015 Edition, except where general terms of ordinary dictionary significance are used.

Botanical classification: *Chrysanthemum* X *morifolium* 'G21VIG05DY'.

Parentage: Naturally-occurring whole plant mutation of *Chrysanthemum* X *morifolium* 'Vigorelli Violet', disclosed in U.S. Plant Pat. No. 23,965.

Propagation:

*Type cutting.*—By vegetative tip cuttings.

*Time to initiate roots, summer.*—About two weeks at temperatures about 20° C.

*Time to initiate roots, winter.*—About 20 days at temperatures about 20° C.

*Time to produce a rooted young plant, summer.*—About 30 days at temperatures about 20° C.

*Time to produce a rooted young plant, winter.*—About 40 days at temperatures about 20° C.

*Root description.*—Fine, fibrous; typically light brown in color, actual color of the roots is dependent on substrate composition, water quality, fertilizer type and formulation, substrate temperature and physiological age of roots.

*Rooting habit.*—Freely branching; medium density.

Plant description:

*Appearance.*—Perennial decorative type *Chrysanthemum* with ligulate-shaped ray florets; stems upright and outwardly spreading giving a uniformly rounded appearance to the plant; plants roughly spherical; very freely branching habit, about 25 primary lateral branches develop, each primary lateral branch with multiple secondary branches; pinching is not required, but enhances lateral branch development; dense and full plant habit; vigorous growth habit and rapid growth rate; plants flexible, not brittle.

*Plant height.*—About 50 cm.

*Plant width.*—About 65 cm.

*Lateral branches.*—Length: About 25 cm. Diameter: About 2 mm to 3 mm. Internode length: About 2 cm to 2.5 cm. Strength: Moderately strong, flexible. Texture: Pubescent, fine; longitudinally ridged. Color: Close to 143B.

*Leaves.*—Arrangement: Alternate, simple. Length: About 5.5 cm to 7 cm. Width: About 3.5 cm to 4 cm. Apex: Rounded to cuspidate. Base: Attenuate. Margin: Palmately lobed and serrate, sinuses between lateral lobes divergent to parallel. Texture, upper and lower surfaces: Slightly pubescent. Venation: Palmately reticulate. Color: Developing leaves, upper surface: Close to 136A. Developing leaves, lower surface: Close to 137A. Fully expanded leaves, upper surface: Close to 136A; venation, close to 148C. Fully expanded leaves, lower surface: Close to 137A; venation, close to 147B to 147C. Petioles: Length: About 1 cm. Diameter: About 2 mm. Texture, upper and lower surfaces: Slightly pubescent; slightly rough. Color, upper surface: Close to 146C. Color, lower surface: Close to 146D. Stipules: Length: About 1 cm. Diameter: About 2 mm. Texture, upper and lower surfaces: Slightly pubescent. Color, upper and lower surfaces: Close to 137A.

Inflorescence description:

*Appearance.*—Decorative type inflorescence form; inflorescences borne on terminals above foliar plane; disc and ray florets arranged acropetally on a capitulum.

*Fragrance.*—Slightly fragrant, pungent.

*Flowering response.*—Under natural season conditions, plants flower during the first two weeks in October in Belgium; flowering response time, about 47 days.

*Postproduction longevity.*—Inflorescences maintain good color and substance for about five weeks; inflorescences persistent.

*Quantity of inflorescences.*—About 20 inflorescences develop per lateral branch.

*Inflorescence buds.*—Height: About 5 mm. Diameter: About 8 mm. Shape: Globular. Color: Close to 21A.

*Inflorescence diameter.*—About 4.5 cm.

*Inflorescence depth (height).*—About 4 cm.

*Disc diameter.*—About 1 mm; inconspicuous.

*Receptacle diameter.*—About 3 mm.

*Receptacle height.*—About 2.5 mm to 3 mm.

*Receptacle shape.*—Raised dome.

*Receptacle color.*—Close to 144B.

*Ray florets.*—Number of ray florets per inflorescence: More than 200 arranged in about ten whorls. Length: About 3 cm to 4 cm. Width: About 6 mm. Shape: Ligulate. Apex: Rounded. Base: Attenuate. Margin: Entire. Aspect: Mostly horizontal. Texture and luster, upper and lower surfaces: Smooth, glabrous; matte. Color: When opening, upper surface: Close to N25D. When opening, lower surface: Close to 15B. Fully opened, upper surface: Center, close to N25D; towards the margins and apex, close to 14B; color becoming closer to 14B with development. Fully opened, lower surface: Close to 9A; color becoming closer to 9C with development.

*Disc florets.*—Number of disc florets per inflorescence: Less than 20 massed at the center of the inflorescence. Length: About 3 mm. Diameter: About 0.5 mm to 1 mm. Shape: Tubular; apices dentate. Texture and luster: Smooth, glabrous; glossy. Color: Apex: Close to 144C. Mid-section: Close to 5B. Base: Close to 145D.

*Phyllaries.*—Number of phyllaries per inflorescence: About 25 arranged in two or three whorls. Length: About 4 mm to 6 mm. Width: About 2 mm to 3 mm. Shape: Ovate. Apex: Rounded. Base: Rounded to truncate. Margin: Entire. Texture, upper and lower surfaces: Smooth, glabrous. Color, upper surface: Close to 137A. Color, lower surface: Close to NN137B.

*Peduncles.*—Length, terminal peduncle: About 4 cm. Length, fourth peduncle: About 6 cm. Length, seventh peduncle: About 8 cm. Diameter: About 2 mm. Angle: About 30° from vertical. Strength: Moderately strong. Texture: Slightly pubescent. Color: Close to 143B.

*Reproductive organs.*—Androecium: Stamen development has not been observed on inflorescences of the new *Chrysanthemum*. Gynoecium: Pistil development has not been observed on inflorescences of the new *Chrysanthemum.*

*Seeds and fruits.*—To date, seed and fruit production have not been observed on plants of the new *Chrysanthemum.*

Garden performance: Plants of the new *Chrysanthemum* have demonstrated excellent garden performance and will tolerate temperatures ranging from about 1° C. to about 45° C.

It is claimed:

1. A new and distinct *Chrysanthemum* plant named 'G21VIG05DY' as illustrated and described.

* * * * *